United States Patent
Shenfarber

(10) Patent No.: US 10,821,299 B1
(45) Date of Patent: *Nov. 3, 2020

(54) TRANSPARENT HEAD FOR A SKIN TREATMENT DEVICE

(71) Applicant: OMM Imports, Inc., Doral, FL (US)

(72) Inventor: Moti Shenfarber, Doral, FL (US)

(73) Assignee: OMM Imports Inc., Doral, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/915,608

(22) Filed: Jun. 29, 2020

Related U.S. Application Data

(63) Continuation of application No. 16/822,702, filed on Mar. 18, 2020, which is a continuation of application No. 16/013,068, filed on Jun. 20, 2018, now Pat. No. 10,625,093.

(51) Int. Cl.
| | | |
|---|---|---|
| *A61N 5/06* | (2006.01) | |
| *A61F 7/00* | (2006.01) | |
| *A61B 18/20* | (2006.01) | |

(52) U.S. Cl.
CPC .............. *A61N 5/0625* (2013.01); *A61F 7/00* (2013.01); *A61N 5/0616* (2013.01); *A61B 18/203* (2013.01); *A61F 2007/0071* (2013.01); *A61F 2007/0086* (2013.01); *A61F 2007/0088* (2013.01); *A61N 2005/0626* (2013.01); *A61N 2005/0632* (2013.01); *A61N 2005/0652* (2013.01); *A61N 2005/0659* (2013.01); *A61N 2005/0662* (2013.01)

(58) Field of Classification Search
CPC ....... A61N 5/0625; A61N 5/0616; A61F 7/00; A61B 18/203
See application file for complete search history.

(56) References Cited

U.S. PATENT DOCUMENTS

| | | | | |
|---|---|---|---|---|
| 8,597,316 | B2 * | 12/2013 | McCombs | A61B 17/1628 606/167 |
| 9,844,622 | B2 * | 12/2017 | Savage | A61M 5/007 |
| 2007/0027443 | A1 * | 2/2007 | Rose | A61B 18/22 606/16 |
| 2014/0150782 | A1 * | 6/2014 | Vazales | A61M 16/0434 128/202.16 |

FOREIGN PATENT DOCUMENTS

WO    WO-2010033630 A1 *   3/2010   ........... A61B 18/203

OTHER PUBLICATIONS

Harrick Optical Materials Archive.org PDF enclosed, https://web.archive.org/web/20090415161723/http://www.harricksci.com/infoserver/optical%20materials.cfm including following links for Quartz Crystal and Sapphire, from Apr. 15, 2009 (Year: 2009).*

* cited by examiner

*Primary Examiner* — Lynsey C Eiseman
(74) *Attorney, Agent, or Firm* — The Concept Law Group, PA; Scott D. Smiley; Scott M. Garrett

(57) ABSTRACT

A transparent cover member for a skin treatment device passes light and heat to a user's skin. The transparent cover member presents a comfortable flat surface at its exterior, and includes features that couple to a heating element that surrounds a plurality of visible light LEDs. The transparent cover member can include retaining features to assist in assembling the head assembly of the skin treatment device.

19 Claims, 10 Drawing Sheets

TRANSPARENT HEAD FOR A SKIN TREATMENT DEVICE

CROSS REFERENCE

This application is a continuation of U.S. application Ser. No. 16/822,702, titled "Therapeutic Device Providing Heat and Light and Head Assembly for Same," and filed on Mar. 18, 2020, which is a continuation of U.S. application Ser. No. 16/013,068, titled "Therapeutic Device Providing Heat and Light and Head Assembly for Same," filed on Jun. 20, 2018, the entireties of each of which are hereby incorporated by reference.

FIELD OF THE INVENTION

The present invention relates generally to skin treatment devices that are used to apply heath and light therapy to the skin of a user, and, more particularly, relates to a transparent head for a skin treatment device that provides both heat and light for treatment of a person's skin.

BACKGROUND OF THE INVENTION

Photo and thermal therapy have long been used to treat skin disorders, as well as for cosmetic purposes. The use of light and heat therapy are recognized to promote blood flow, nerve stimulation, muscle relaxation, and can improve and maintain complexion to reduce wrinkling caused by environmental and other stresses experienced by the skin. Furthermore, the use of light and heat therapy is also recognized to be useful in treating and preventing certain skin conditions.

Accordingly, there are a wide variety of devices on the market that provide heat and/or light that are configured to be used on a person's skin, particularly on the face. These devices have varying efficacy, ranging from being essentially ineffective at all, to potentially unsafe if used improperly. A number of these devices have been designed for home, private use. Accordingly, it is important to ensure that such devices operate safely, while providing the expected benefit. From a manufacturing standpoint, it is also important to reduce the manufacturing costs associated with manufacturing these devices.

Therefore, a need exists to overcome the problems with the prior art as discussed above.

SUMMARY OF THE INVENTION

The invention provides a transparent cover member or head for a skin treatment device that overcomes the hereinafore-mentioned disadvantages of the heretofore-known devices and methods of this general type.

In accordance with some embodiments of the inventive disclosure, there is provided a transparent cover member for a skin treatment device that includes a top having a front and a back, with the front being flat and configured to face outward from the skin treatment device, and the back being opposite the front. Further, the back includes a central portion and an outside wall extending down from the front, around an entirety of a perimeter of the front. The back of the transparent cover member has an outside shoulder formed at a bottom of the outside wall. The outside shoulder extends inward from the bottom of the outside wall inward to an inner edge of the of the outside shoulder that meets a standoff wall of a standoff portion. The standoff portion extends downward away from the front and surrounding the central portion, and the outside shoulder surrounds the standoff portion. The back further includes an inner shoulder formed at an inside of the standoff portion above the bottom of the standoff portion and which extends inward to an inner edge of the inner shoulder. The inner edge of the inner shoulder terminates at an inner wall which extends upwards to an inner surface of the top in the central portion. The standoff portion surrounds the inner shoulder and extends downward, with respect to the front, farther than both the outside shoulder and the inner shoulder, and the inner shoulder is lower than the inner surface of the front and surrounds the inner surface of the top.

In accordance with another feature, the transparent cover member is comprised of sapphire glass.

In accordance with another feature, the transparent cover member is comprised of silicon.

In accordance with another feature, wherein the transparent cover member further comprises, on the back, an ultrasonic coupling feature extending from the back in the central portion.

In accordance with another feature, the transparent cover member is comprised of material that is selected to be less transparent for some wavelengths of infrared light while being more transparent for other wavelengths of infrared light.

In accordance with another feature, a surface of front of the transparent cover member is frosted.

In accordance with another feature, the transparent cover member further includes a plurality of retention features that protrude outward from the standoff wall.

In accordance with another feature, the plurality of retention features are formed in a ramp configuration.

In accordance with some embodiments of the inventive disclosure, there is provided a transparent cover member for a skin treatment device that provides light and heat therapy to a user's skin that includes a flat front configured to face outward from the skin treatment device. The transparent cover member also includes a back that is opposite the flat front, and has a central portion. There is further included an outside wall of the transparent cover member that extends down from the front around the entire perimeter of the front. There is further included an outside shoulder formed at a bottom of the outside wall. The outside shoulder extends inward from the outside wall to an inner edge of the of the outside shoulder, which meets a standoff wall of a standoff portion. The standoff portion extends downward from the inner edge of the outside shoulder in a direction away from the front. The standoff portion surrounds the central portion and the outside shoulder surrounds the standoff portion. There is further included an inner shoulder formed at an inside of the standoff portion above a bottom of the standoff portion. The inner shoulder extends inward from the standoff portion to an inner edge of the inner shoulder. The inner edge terminates at an inner wall which extends upwards to an inner surface of the central portion. The standoff portion surrounds the inner shoulder and extends downward, with respect to the front, farther than both the outside shoulder and the inner shoulder. The inner shoulder is lower than the central portion and surrounds the central portion.

In accordance with another feature, the transparent cover member is comprised of sapphire glass.

In accordance with another feature, the transparent cover member is comprised of silicon.

In accordance with another feature, the transparent cover member is comprised of material that is selectively transparent for selected wavelengths of infrared light.

In accordance with another feature, a surface of the flat front and a surface of the outside wall are frosted.

In accordance with another feature, the transparent cover member further includes a plurality of retention features that protrude outward from the standoff wall.

In accordance with another feature, the plurality of retention features are formed in a ramp configuration.

In accordance with some embodiments of the inventive disclosure, there is provided a monolithic glass head for a skin treatment device that includes a flat front portion having a front surface that is configured to face outward from the skin treatment device. There is further included a back portion that is opposite the flat front portion and which includes a central portion, and an outside wall portion extending down from the flat front portion around an entirety of a perimeter of the flat front portion. There is further included an outside shoulder, formed at a bottom of the outside wall portion, which extends inward from the outside wall to a standoff wall of a standoff portion, wherein the outside shoulder surrounds the standoff portion. The standoff portion extends downward, in a direction away from the flat front portion, and surrounds the central portion of the back portion. There is further included a plurality of retention features that protrude outward from the standoff wall, and an inner shoulder formed at an inside wall of the standoff portion above a bottom of the standoff portion, and which extends inward to an inner edge of the inner shoulder, wherein the inner edge of the inner shoulder terminates at an inner wall which extends upwards to the central portion of the back portion, wherein the standoff portion surrounds the inner shoulder and extends downward, with respect to the front surface, farther than both the outside shoulder and the inner shoulder.

In accordance with another feature, the transparent cover member consists entirely of sapphire glass or silicon.

In accordance with another feature, the top of the transparent cover member is frosted.

In accordance with another feature, the plurality of retention features are formed in a ramp configuration.

In accordance with another feature, the transparent cover member is comprised of material that is selected to be less transparent for some wavelengths of infrared light while being more transparent for other wavelengths of infrared light.

Although the invention is illustrated and described herein as embodied in a transparent cover member for a skin treatment device, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the head of the skin treatment device. Those skilled in the art can understand the specific meanings of the above-mentioned terms in the embodiments of the present invention according to the specific circumstances

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
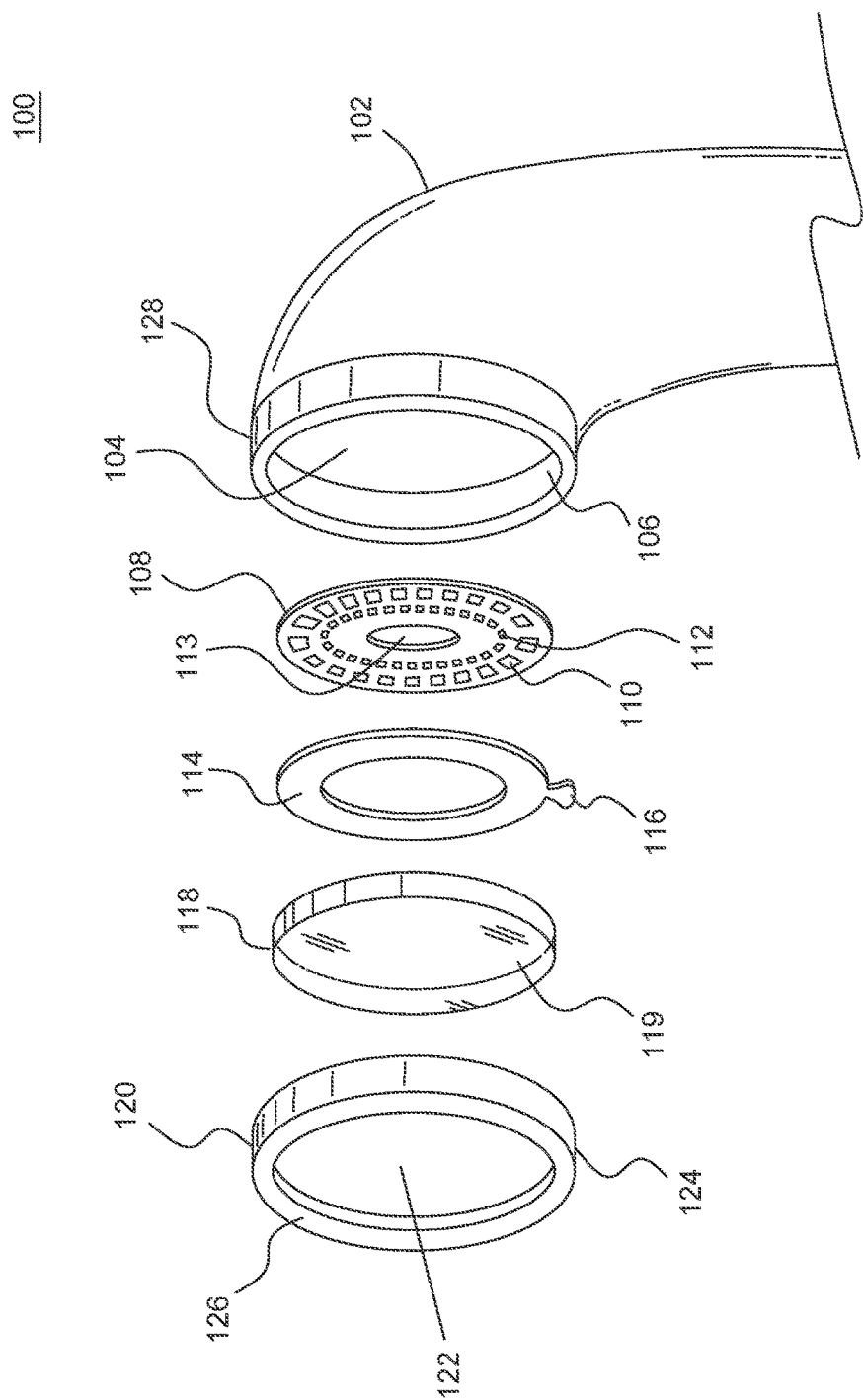
FIG. 1 is an exploded perspective view of a head assembly for a skin treatment device, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

Embodiments of the invention solve the problems associated with the prior art by providing a transparent head or cover member for a skin treatment device with two sets of LEDs, where the visible light LEDs are surrounded by thermal infrared LEDs. The heat output can be controlled using both the infrared LEDs and with a heat element disposed adjacent the transparent cover member. The inventive cover member reduces manufacturing costs, as well as improves the delivery of light and heat to a user's skin under control of the user.

FIG. 1 is an exploded perspective view of a head assembly 100 for a skin treatment device, in accordance with some embodiments. The head assembly is assembled into the head 102 of a skin treatment device. The skin treatment device further includes a body in which other components of the skin treatment device can be located, including, for example, batteries, control circuitry, interface components like buttons, switches, and so on. At the front of the head 102 is an opening 104 in which the head assembly 100 is assembled. In some embodiments an shoulder 106 can be formed around the perimeter, or portions of the perimeter, to support the component of the head assembly 100.

The head assembly includes a circuit board 108 that can be shaped substantially the same as the opening 104, and on which there is disposed at least two different, independent series of light emitting diodes (LEDs). A first series of LEDs, such as LED 110, can be arranged around the perimeter of the circuit board 108, on the front of the circuit board 108. The first series of LEDs can all be thermal infrared LEDs. That is, the first series of LEDs are primarily used to generate heat radiation in the form of infrared light of a particular infrared wavelength range. The LEDs of the first series of LEDs may also produce some visible light in some embodiments. When the head assembly is formed in a circular shape, the first series of LEDs can form a circle around the periphery of the front of the circuit board 108. A second series of LEDs can be disposed on the front of the circuit board 108 in an arrangement that follows the first series of LEDs, but between the first series of LEDs and a center portion of the circuit board. In embodiments where the head assembly 100 is formed in a circular shape, the second series of LEDs can be arranged on a circle that is concentric with a circle on which the first series of LEDs is arranged. The second series of LEDs can be configured to generate visible light in one or more colors. For example, the second series of LEDs can be configured to produce red or blue light, selectively. In some modes the second series of LEDs can produce red light, and in some modes they can produce blue light. Furthermore, it is contemplated that the second series of LEDs can include one or more LEDs for producing ultraviolet light, or at least light that includes light in the ultraviolet portion of the light spectrum. Accordingly, the second series of LEDs can include two or more separately controlled LEDs, each for producing different colors, and which can be selectively enabled to emit their respective color light based on a mode of operation of the skin treatment device. The circuit board 108 can further include an opening 113, through which other portions of the skin treatment device can pass to engage other components of the head assembly 100.

Over the circuit board 108, arranged to be over the first series of LEDs, is a heat element 114. The heat element 114 can be either an active or a passive element, and generally includes a metal or metalized outer surface, at least on a top region (i.e. facing outwards from the device). As a passive device the heat element 114 acts as a heat spreader, to prevent hot spots at the face of the head assembly 100 during use. As an active device, the heat element 114 can include an electrically resistive component which can be used to generate heat. A tab 116 of the heat element 114 can include leads that can connect to the circuit board 108 so that an electric current can pass through the resistive component of the heat element 114 to generate heat, as desired, under control of skin treatment device.

A transparent cover member 118 fits over the heat element 114 and circuit board 108, and is comprised of a transparent material that can be selectively emissive for particular light wavelengths. For example, the transparent cover member 118 can be comprised of a material that blocks or attenuates certain infrared wavelengths. For example, the transparent cover member 118 can be made of sapphire glass, silicon, chalcogenide glass, or polymeric materials. The front 119 of the transparent cover member 118 is generally flat, although it can be made convex as well, as it will be pressed against a user's skin. The back of the transparent cover member 118, opposite the front 119, is stepped with concentric portions having different thicknesses to the front 119, as will be shown.

A metal bezel 120 encircle the head assembly 100 and hold it into the opening 104 of the head 102 of the skin treatment device. The metal bezel 120 has an opening 122 that constitutes the majority of the front area of the metal bezel 120, through which the front 119 of the transparent member 118 can be seen, and therefore all of the light generated by the LEDs on the circuit board 108. The bezel 120 includes a rim 126 over the periphery of the front, around the opening 122, and a side 124 that extends down from the front, around the perimeter of the front of the bezel 120. The side 124 goes over an outside portion 128 of the head of the skin treatment device. The bezel 120 and the transparent member 118 can be mounted on the head 102 of the skin treatment device such that they can move together, with respect to a direction normal to the front 119 of the transparent member to allow touch sensing by the skin treatment device. That is, the transparent member 118 and/or the bezel 120 can be mechanically coupled to a switch which is closed (or opened) when the user presses the front 119 of the transparent member against their skin. The switch can be a mechanical switch that physically opens/closes and electrical circuit, or it can be a capacitive sensor that detects a change in capacitance at the metal bezel 120, as occurs when the user presses the front of the head assembly against their skin.

Figure 2:
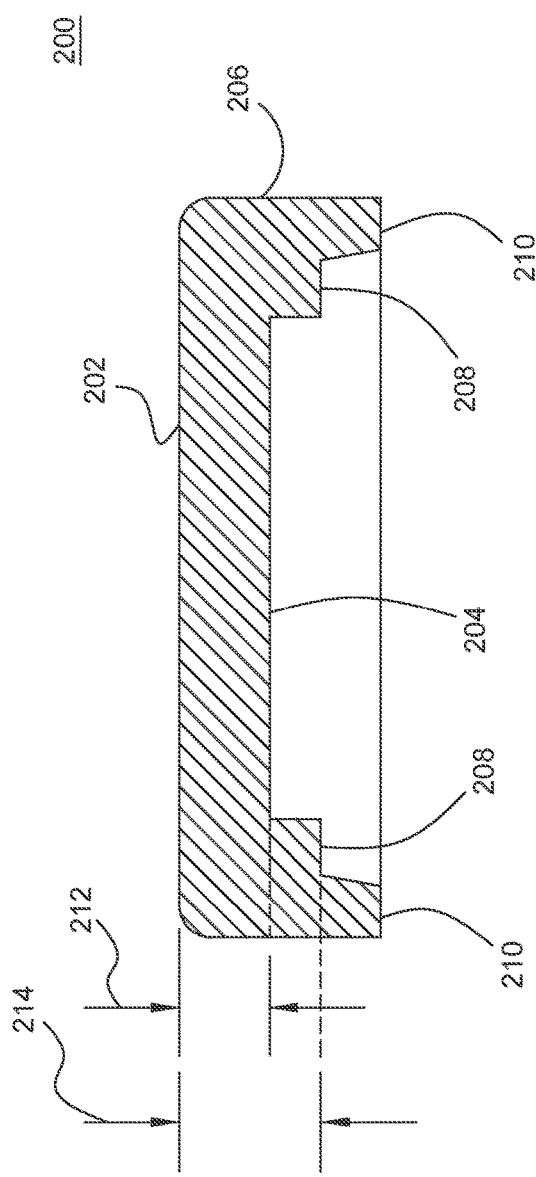
FIG. 2. is a side cut away view of a transparent cover member for a head assembly of a skin treatment device, in accordance with some embodiments.

FIG. 2. is a side cut away view of a transparent cover member 200 for a head assembly of a skin treatment device, in accordance with some embodiments. The transparent cover member 200 can be substantially the same as transparent cover member 118 of FIG. 1, in some embodiments. As shown here, the front 202 is at the top of the drawing, and a back 204 is opposite the front 202. The distance through the material directly from the front 202 to the back 204 is a first thickness 212. The back 204 is sized to correspond with the visible light LEDs so that light from the visible LEDs is transmitted through the transparent cover member 200 from the back 204 to the front 202. Around the perimeter of the main back section 204 is a perimeter shoulder 208 that has a different thickness 214 to the front 202. The perimeter shoulder 208 is sized and shaped to correspond to the size and shape of the heat element (e.g. 114), which sits between the perimeter shoulder 208 and the infrared LEDs on the circuit board. Around the perimeter shoulder 208 is a standoff 210 that is thicker than either the back 204 or perimeter shoulder 208 that is sized and shaped to sit on the perimeter of the circuit board, or other support structure, and which meets the side 206 of the transparent cover member.

Figure 3:
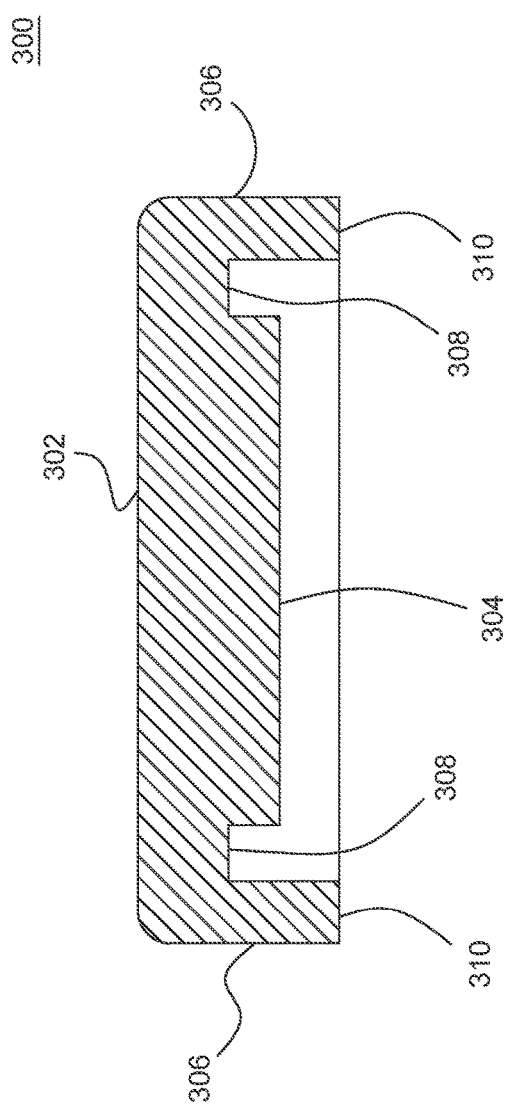
FIG. 3 is a side cut away view of a transparent cover member for a head assembly of a skin treatment device, in accordance with some embodiments.

FIG. 3 is a side cut away view of a transparent cover member 300 for a head assembly of a skin treatment device, in accordance with some embodiments. Similar to transparent cover member 200, the embodiments represented by transparent cover member 300 include a front 302 and a back portion 304 that is opposite the front 302. Visible light from LEDs on the circuit board of the head assembly passes through the transparent cover member 300 from the back 304 to the front 302, and is emitted from the front. However, in embodiments consistent with that shown here, the perimeter shoulder 308 is less thick to the front 302 than the back portion 304. In some embodiments the infrared LEDs may be taller than the visible light LEDs, thus, and higher clearance of the perimeter shoulder 308 is needed for the heat element and infrared LEDs. The perimeter shoulder 308 is formed around the perimeter of the back 304, and is itself surrounded by the standoff 310, which is contiguous with the side 306 of the transparent cover member 300.

Figure 4:
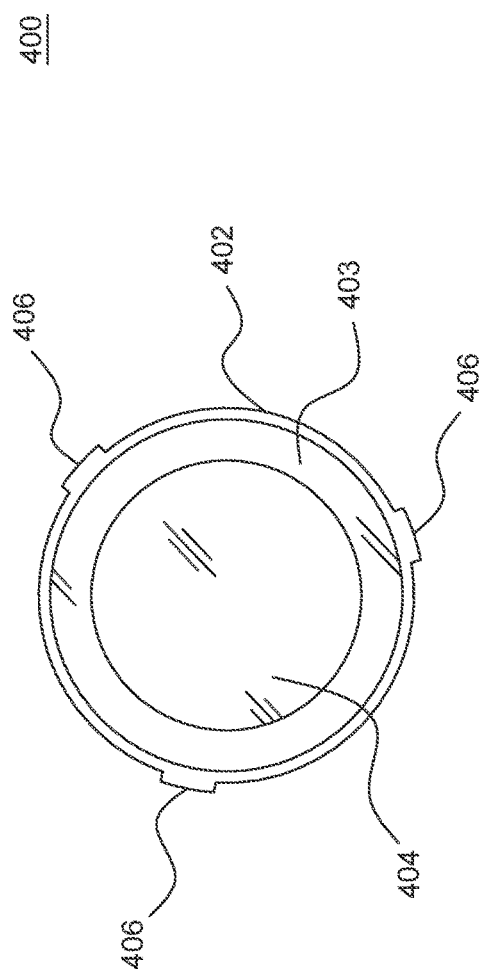
FIG. 4. shows a bottom view of a transparent cover member having lugs for holding the head assembly together in the body of a skin treatment device, in accordance with some embodiments.

FIG. 4. shows a bottom view of a transparent cover member 400 having lugs 406 for holding the head assembly together in the body of a skin treatment device, in accordance with some embodiments. In this view of the bottom, it can be seen that the transparent cover member 400 is circular, and has a standoff 402 at the outermost radius around the transparent cover member 400. Inside the standoff 402 is a perimeter shoulder 403 in which the heat element can be disposed. The remainder of transparent cover member shown is the back 404 through which the visible LEDs shine to emit visible light. The lugs 406 can be disposed at several positions around the outside, on the side of the transparent cover member 400. The lugs 406 can be formed as a protruding portion of the material of the transparent cover member and are sized and shaped to engage a corresponding retention feature in the head of the skin treatment device. So, for example, the transparent cover member 400 can be placed into the front opening (e.g. 104 of FIG. 1), where channels formed in the inside wall of the housing of the skin treatment device head receive the lugs, and once the transparent cover member 400 is fully inserted, it is turned (e.g. clockwise) such that the lugs 406 engage transverse channels to retain transparent cover member 400 in place, with the standoff 402 bearing against the circuit board (e.g. 108) to likewise hold it in place. Then the bezel (e.g. 120) can be placed over the assembly.

Figure 5:
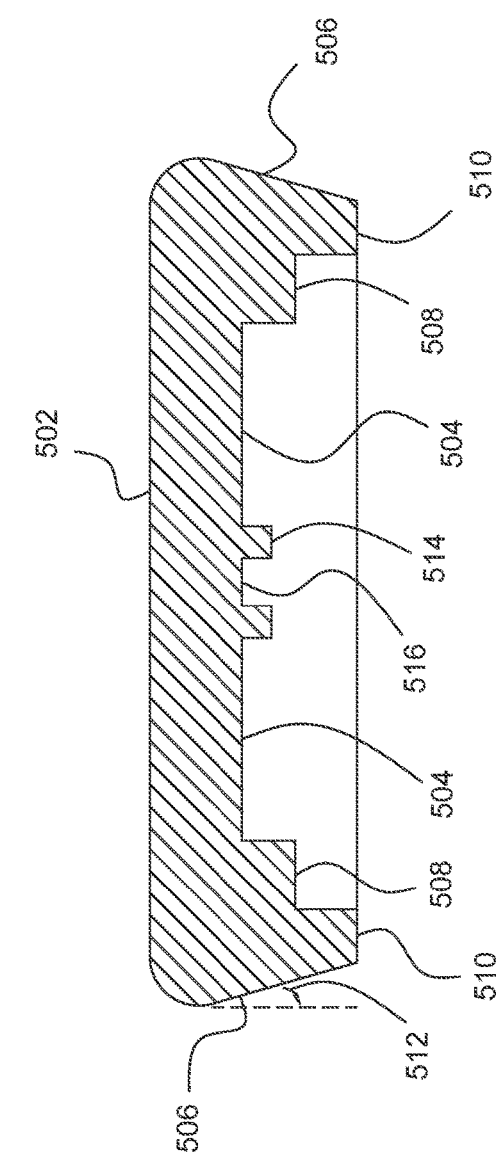
FIG. 5 shows a side cut away view of a transparent cover member for a head assembly of a skin treatment device, including an ultrasonic coupling feature, in accordance with some embodiments.

FIG. 5 shows a side cut away view of a transparent cover member 500 for a head assembly of a skin treatment device, including an ultrasonic coupling feature, in accordance with some embodiments. It is contemplated that a sonic or ultrasonic driver can be coupled to the transparent cover member 500 to impart vibration into the user's skin when using the skin treatment device, and thereby promote blood flow in the user's skin. The front 502 is a major surface the faces outward from the skin treatment device, and makes contact with the user's skin. Opposite the front is the back 504, which is surrounded by a perimeter shoulder 508, which in turn is surrounded by a standoff portion 510. Unlike previously described embodiments of the transparent cover member, however, the sides 506 are angled inward from front to back and an angle 512 from vertical (i.e. normal to the plane of the front surface 502). By angling the sides as such, at an angle of 15 to 45 degrees, the transparent cover member can be more effective at emitting infrared light through the front 502 into the user's skin. Furthermore, an ultrasonic coupling feature can be formed in the center of the back 504 by an annular ridge 514 the forms a pocket 516 in which the tip of an acoustic driver can be positioned to impart vibration and audio or ultrasonic frequencies into the transparent cover member 500 and thereby to the skin of the user.

Figure 6:
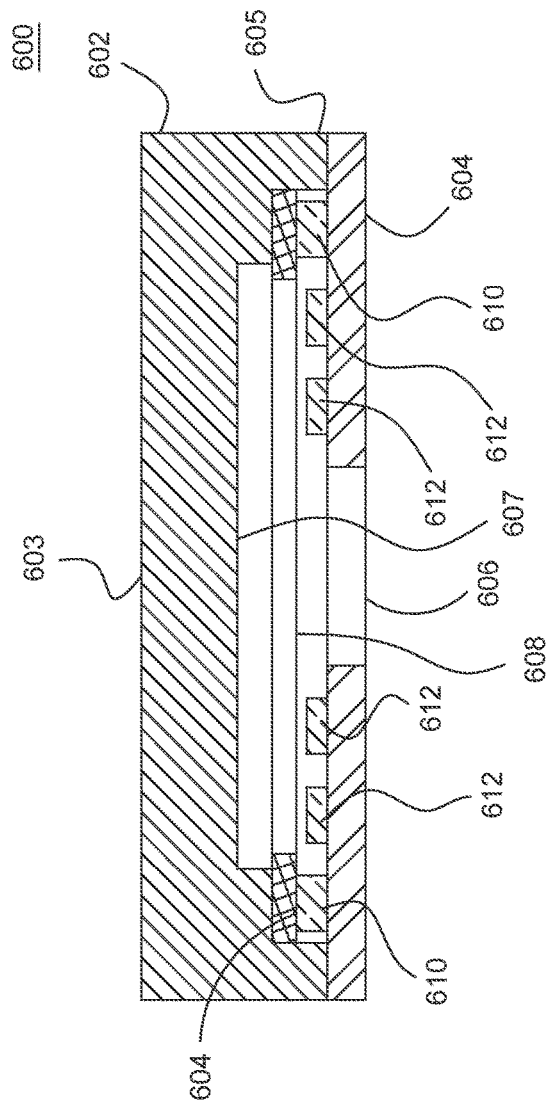
FIG. 6 is a side cut away view of an assembled head assembly, in accordance with some embodiments.

FIG. 6 is a side cut away view of an assembled head assembly 600, in accordance with some embodiments. This view does not show the housing of the skin treatment device, just the main components of the head assembly when put together as they would be when assembled into the head of the skin treatment device. A transparent cover member 602 having a front 603 rests on a circuit board 604 at the standoff 605 of the transparent cover member, which is on the outermost portion at the back of the transparent cover member 602, opposite the front 603. The circuit board 604 may include a hole or aperture 606 in the center of the circuit board 604. On the circuit board are several visible light LEDs 612 in a first series of LEDs which produce light that passes through the transparent cover member 602 from the back 607 to the front 603. Around the outside region of the circuit board 606 where the visible light LEDs 612 are disposed is a heat element 608 corresponding to a perimeter shoulder 609 of the transparent cover member 602. The heat element 608 can be provided over the infrared LEDs 610 to emit infrared light into the heat element. In some embodiments, at least some of the infrared LEDs 610 can be positioned to emit light through the back 607 to the front 603 as well. The assembly shown here can vary, in other embodiments, to accommodate or include the variations described and shown in any of the preceding drawings as well.

Figure 7:
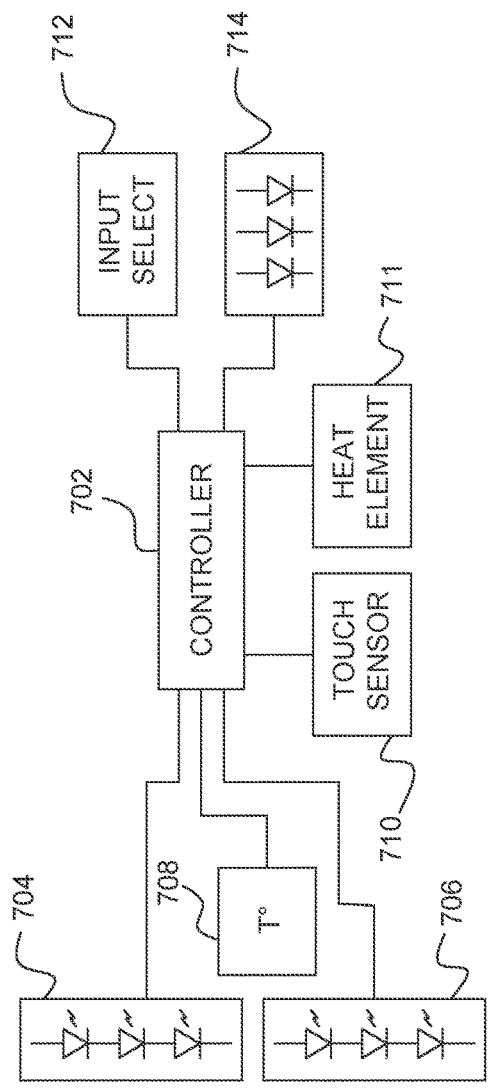
FIG. 7 is a block schematic diagram of some electronic and electric components of a skin treatment device, in accordance with some embodiments.

FIG. 7 is a block schematic diagram of some electronic and electric components of a skin treatment device 700, in accordance with some embodiments. In generally a controller or control circuit 702 controls the electrical operation of the skin treatment device. The controller 702 can be, for example, a logic circuit or a microcontroller that operates according to instruction code. The controller 702, for example, controls the operation of a first series of LEDs 704 and a second series of LEDs 706, which can be, for example, a series of visible light LEDs and a series of infrared LEDs, respectively. To control each series, a control signal can be provided to a switching transistor to turn the LEDs on or off, accordingly. A heat element 711 can likewise be enabled or disable to provide heat, based on a user input 712. The user input 712 can be, for example, one or more buttons that the user operates to indicate the desired operation of the skin treatment device. Several indicator LEDs 714 can be controlled to indicate the mode of operation selected by the user. Each of the selector LEDs 714 can be individually turned on or off by the controller 702, according to the selected mode of operation.

Several safety features can be included, such as a temperature sensor 708 which indicate a temperature of the transparent cover member to the controller 702. If the indicated temperature reaches a maximum threshold, then the controller 702 can turn off the heat element 711 and/or the infrared LEDs 706. A touch sensor 710 can indicate to the controller 702 when the user has touched the head to the user's skin. The touch sensor 710 can be a switch that is closed when the user presses the head of the skin treatment device to their skin, or a capacitive sensor coupled to the head assembly (e.g. at the metal bezel), to sense a change in capacitance, as occurs when the head touches the user's skin. Accordingly, when the user selects a mode of operation, the controller can refrain from activating the LEDs 704, 706 and heat element (if it is an active heat element), according to the selected mode of operation, until the user touches the head of the skin treatment device to their skin, or at least until the controller receives an indication of such from the touch sensor.

Figure 8:
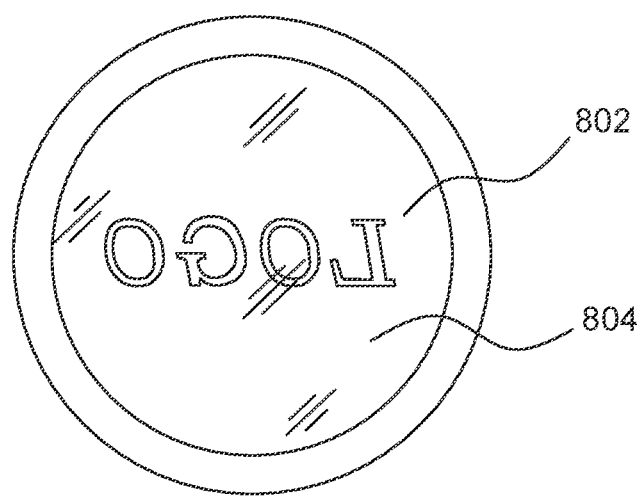
FIG. 8 is a bottom view of a transparent cover member having artwork etched into the back side of the transparent cover member, in accordance with some embodiments.

FIG. 8 is a bottom view of a transparent cover member 800 having artwork 802 etched into the back side of the transparent cover member 800, in accordance with some embodiments. The artwork 802 can be etched on the back 804 of the transparent cover member 800 to create a translucent surface in the artwork, rather than a transparent surface, on the back 804 of the transparent cover member 800. Thus the artwork will be visibly distinct from the surrounding transparent regions, and will be illuminated by the visible light of the LEDs. The artwork can be, for example, a logo or wording associated with the maker of the skin treatment device.

Figure 9:
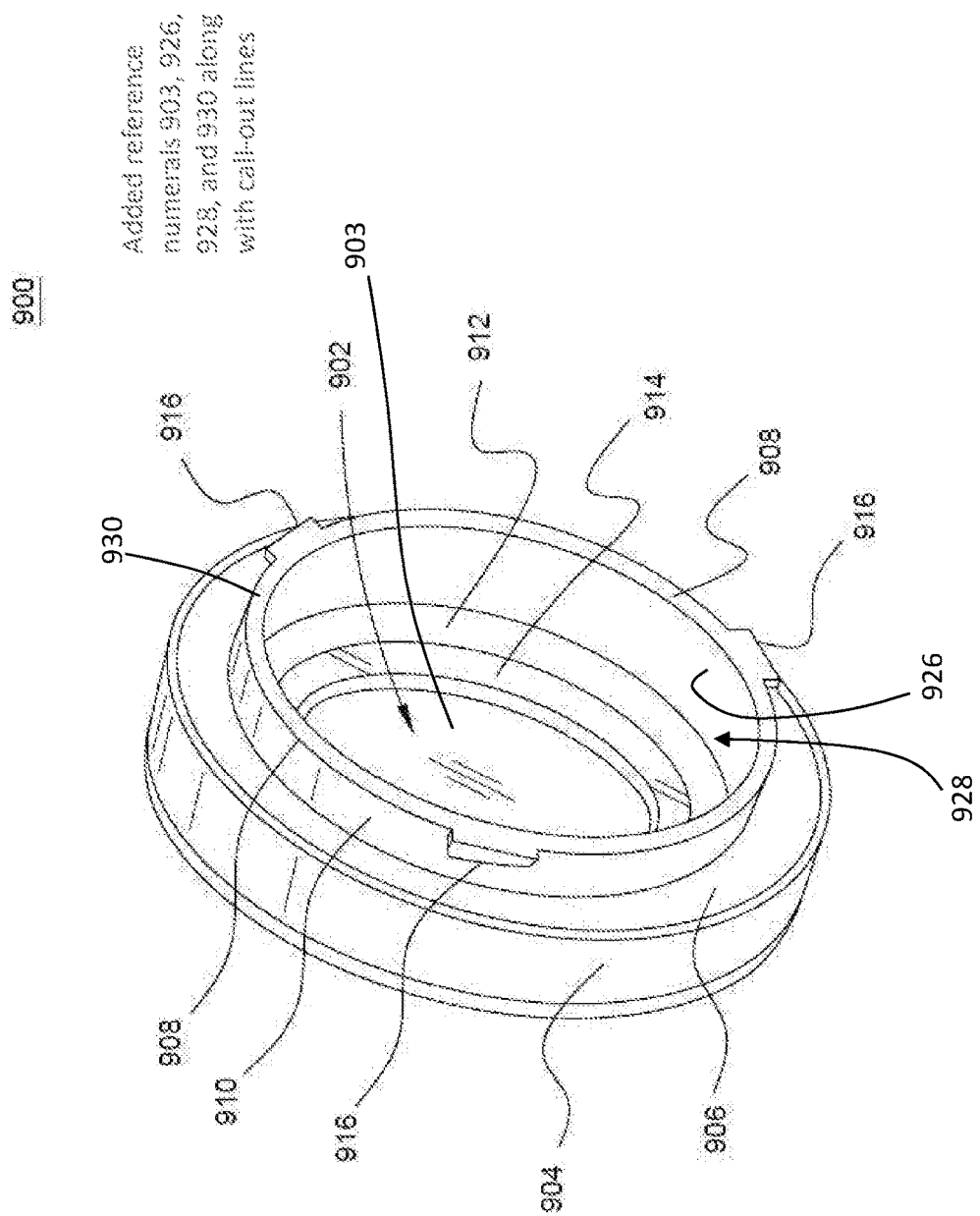
FIG. 9 is an isometric view of a transparent cover member from the side and rear, in accordance with some embodiments.
Figure 10:
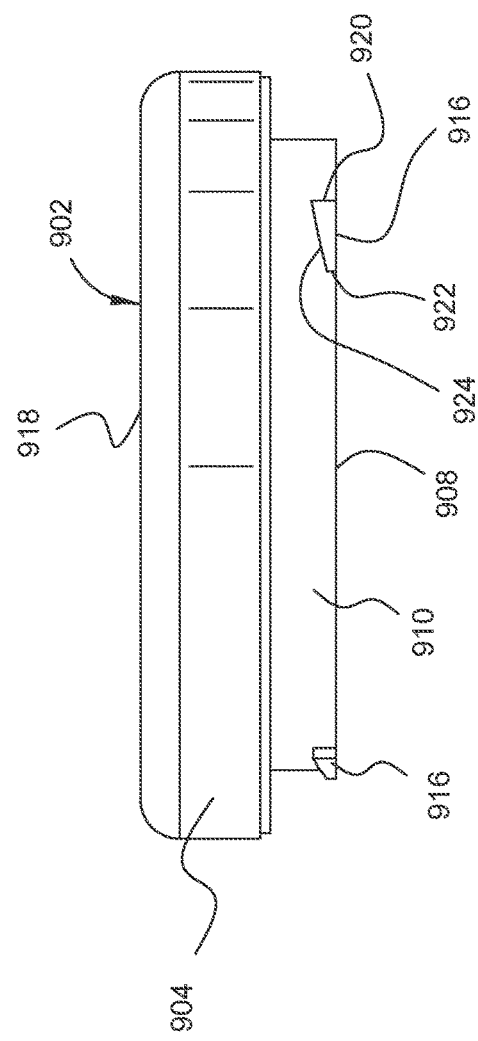
FIG. 10 is a side elevational view of a transparent cover member as depicted in FIG. 9, in accordance with some embodiments.
Figure 11:
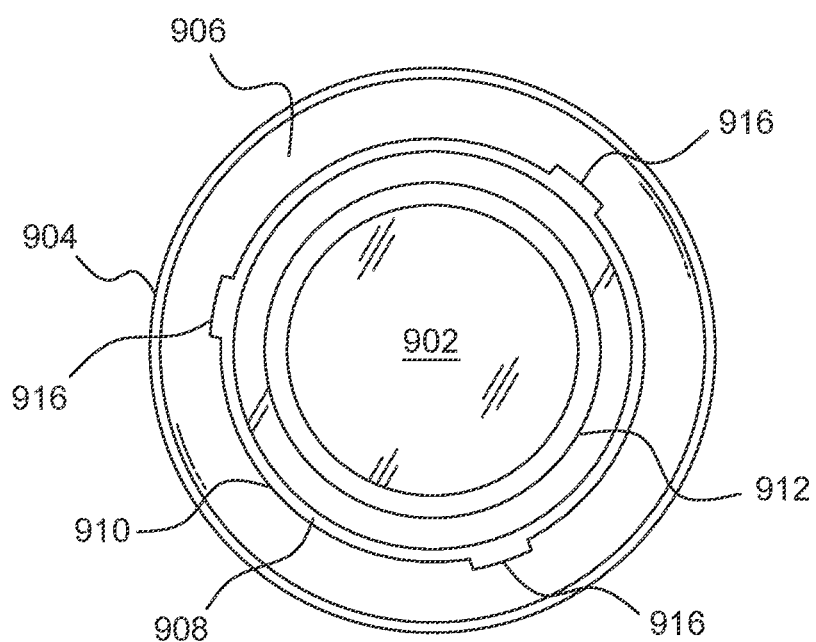
FIG. 11 is a bottom plan view of a transparent cover member as depicted in FIG. 9, in accordance with some embodiments.
Figure 12:
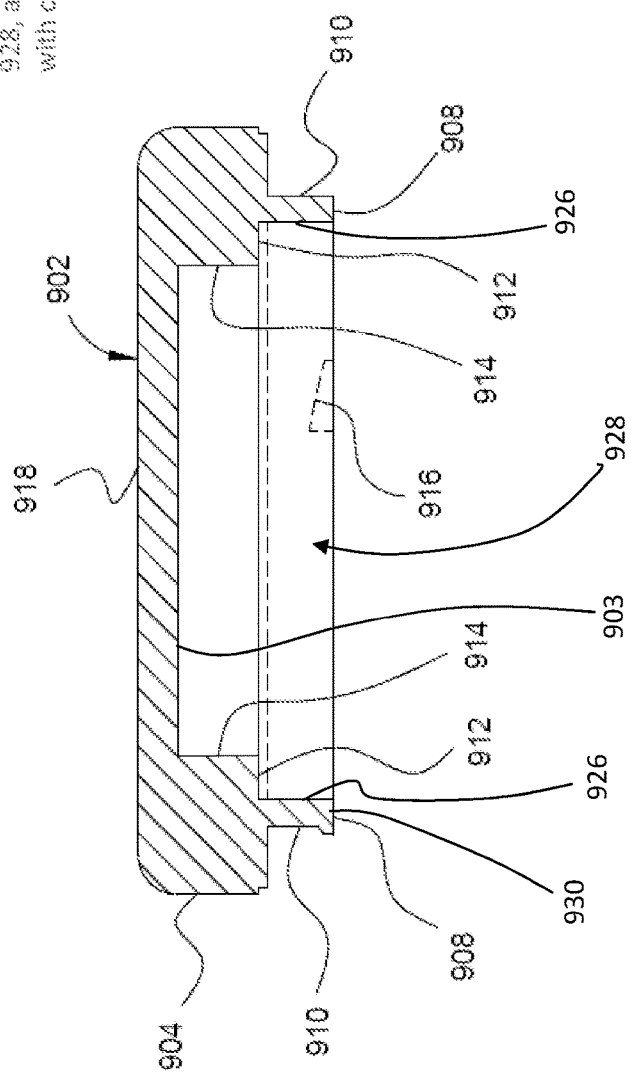
FIG. 12 is a side cut-away view of a transparent cover member as depicted in FIG. 9, in accordance with some embodiments.

FIG. 9 is an isometric view of a transparent cover member 900 from the side and rear, in accordance with some embodiments. FIGS. 10-11 also show the transparent cover member from different angles. FIG. 12 shows a side cutaway view of the transparent cover member 900. Accordingly, the reference numerals pointing to the same structure in FIGS. 9-12 are carried forward through all these drawings.

The transparent cover member 900 is made of a transparent material, such as sapphire glass, polymer, silicon (e.g. silicon nitride), or any other suitable transparent material. The transparent cover member 900 has a top 902, which, in the view of FIG. 9, the inside surface of the top 902 is seen. Around the outside of the transparent cover member 900, is an outside wall 904 that extends from the outer perimeter of the upper surface or front (918) of the top 902, and generally downwards. At the bottom of the outside wall 904 is an outside shoulder or ledge 906 at a substantial angle (e.g. 90 degrees) to the outside wall 904. An inner edge of the outside shoulder 906 meets a standoff wall 910 of the standoff portion 908 which extends downward. The standoff portion 908 defines the outside from the inside of the transparent cover member 900. The standoff portion 908 surrounds the central portion 903 of the transparent cover member 900 at the back of the top 902, which is inside of the transparent cover member 900. From the inside of the standoff portion 908, extending inward at a substantial angle from the inner wall of the standoff, is an inner shoulder 912. The outside of the standoff wall 910 has a diameter that is smaller than the diameter of the front face (top 902). The standoff portion has an inner standoff wall 926 that extends perpendicular to a plane defined by the front 918 from the bottom 930 of the standoff wall to a height that is above the outer shoulder 906. A hollow space 928 is defined and bounded by the inner standoff wall and the central portion 903 of the back. The inner shoulder 912 can be adjacent or in contact with a ring-shaped heating element, as discussed in FIGS. 1 & 6. The inner shoulder 912 terminates at an inner edge, at which an inner wall 914 extends to the inside surface of the top 902. The inner wall 914 defines the region in which the visible light LEDs are arranged so that their light can pass through the top 902.

At two or points at the bottom of the standoff portion 908, on the outside of the standoff wall 910, there are retention features 916 which engage corresponding retention features in the inside of the housing of the skin treatment device to retain the transparent cover member 900 in the housing of the skin treatment device. The retention features 916 protrude outward from the standoff wall 910 and can be ramped or inclined, where one end 922 (along the wall 910) of the protrusions is lower (relative to the top 902) than the other end 920, forming a ramped top 924 of the protrusion 916.

In some embodiments the outer surface 918 of the top, or the inside surface (or both) of the transparent cover member 900 can be treated to be translucent, rather than transparent. For example, the outer surface 918 can be acid treated or sanded/sand blasted to create a frosted effect. A translucent treatment obscures the circuitry and LEDs from view while still allowing most of the light produced by the LEDs to shine out of the transparent cover member 900. This treatment give the surface a frosted appearance, as is known in the art.

Figure 13:
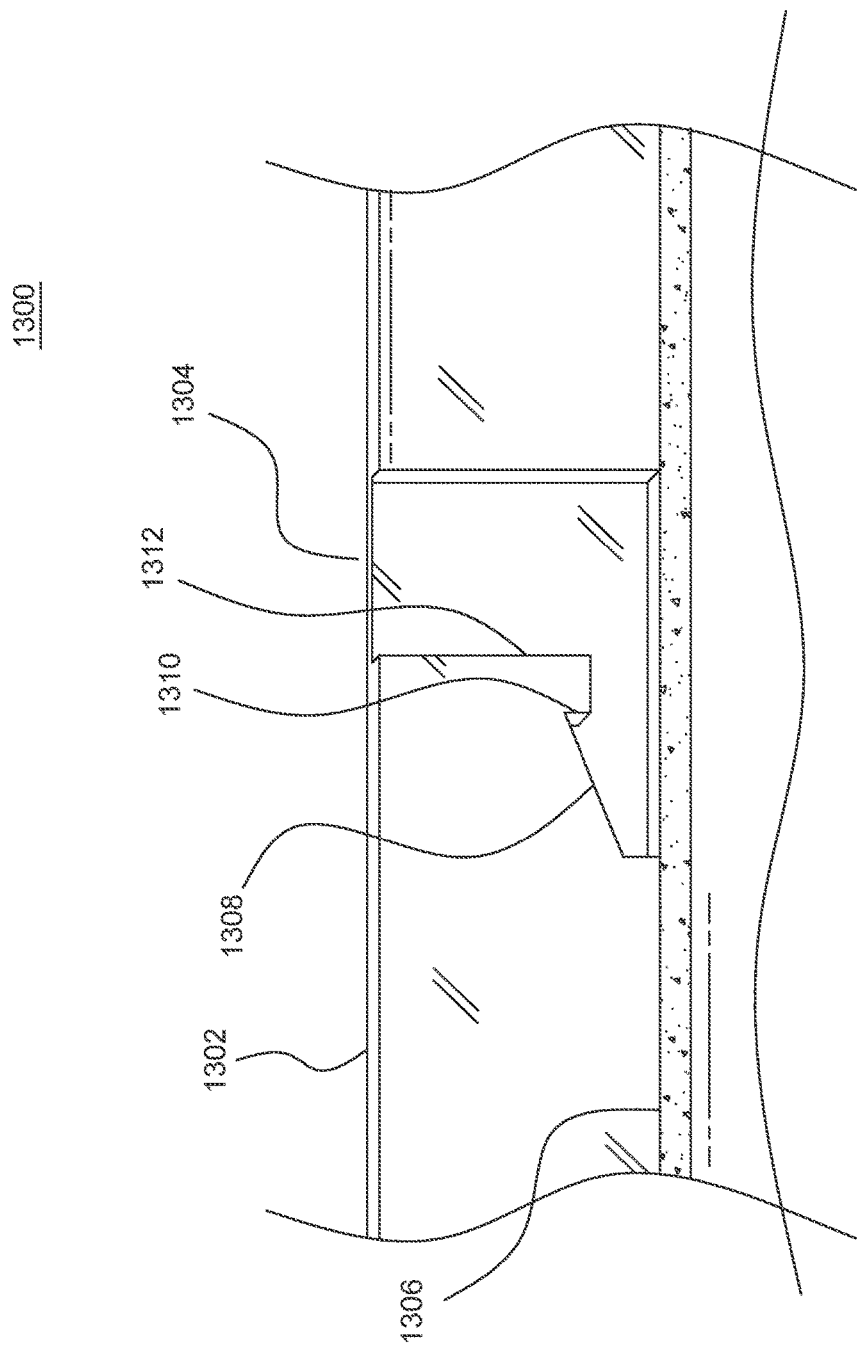
FIG. 13 is a side view of the inside of the top portion of a housing for an skin treatment device, showing the retention feature for engaging a corresponding retention feature of a transparent cover member, in accordance with some embodiments.

FIG. 13 is a side view of the inside of the top portion of a housing 1300 for an skin treatment device, showing the retention feature for engaging a corresponding retention feature of a transparent cover member, in accordance with some embodiments. The view shown here is a slight isometric view to show one alternative retention feature. The retention feature is intended to engage a retention feature such as protrusions 916 on the transparent cover member 900. Accordingly, a vertical channel 1304 is formed in the inner surface of the housing 1300, starting at a top edge 1302 and being formed downward from the top edge 1302. The channel 1304 is a portion where the all of the housing 1300 is thinner than the surrounding portions of the housing 1300, giving clearance for a protrusion as the transparent housing member is lowered into the housing 1300 from the top. At the bottom of the channel 1304 can be a compliant or slightly compressible material 1306 on a shoulder of ledge in the housing 1300, and that the bottom of the protrusion 916 will contact. Upon making contact, the higher end (e.g. 920) of the protrusion 916 will be higher than an interference portion 1312. As the transparent cover member is rotated, the interference portion 11312 can slide along the ramped top (e.g. 924) and the protrusion, causing the compressible material 1306 to be compressed until the higher end passes the interference portion 1312, and the higher end of the protrusion is then on the inside 1310 of the interference portion 1312, at which point the compressible material 1306 pushes or urges the transparent cover member slight upwards, causing the higher end of the protrusion to be captured by the interference portion 1312, with the protrusion fitting within a pocket 1308. Thus, the transparent cover member will be retained until the transparent cover member is again pressed downward, compressing the compressible material 1306, so that the higher end of the protrusion can pass under the interference portion 1312, allowing the transparent cover member to be rotated in the reverse direction such that the protrusion is then located in the channel 1304, allowing the transparent cover member to be removed from the housing 1300.

The inventive embodiments described herein provide an improved head assembly for a skin treatment device for providing light and heat therapy to a user's skin. The embodiments provide a simplified assembly while also providing optimized output characteristics to control the heat and light output as desired by each different user. In particular, embodiments provide the benefit of providing heat and light through a monolithic transparent cover member that can also include retention features that make assembly/disassembly simple, reducing manufacturing costs while also improving the output sensitivity experienced by a user.

What is claimed is:

1. A transparent cover member for head assembly of a skin treatment device, comprising:
    a top having a front and a back;
    the front being flat, defining a front plane, and configured to face outward from the skin treatment device;
    the back being opposite the front and having:
        a central portion;
        an outside wall extending down from the front, around an entirety of a perimeter of the front;
        the back of the top having an outside shoulder formed at a bottom of the outside wall, the outside shoulder extending inward from the bottom of the outside wall inward to an inner edge of the outside shoulder, wherein the inner edge of the outside shoulder meets an standoff wall of a standoff portion; and
        the standoff portion extending downward away from the back of the top and surrounding the central portion, the standoff portion having an inner standoff wall that extends to a bottom of the standoff in a direction that is perpendicular to a plane of the front, wherein the inner standoff wall of the standoff portion surrounds and defines a hollow space at the back of the transparent cover member that is bounded by the inner standoff wall and the back of the top;
        wherein the outside shoulder surrounds the standoff portion;
        wherein the standoff portion extends downward, with respect to the front, farther than the outside shoulder; and
        wherein the top, back, and standoff portion are made of a transparent material.

2. The transparent cover member of claim 1, wherein the transparent cover member is comprised of sapphire glass.

3. The transparent cover member of claim 1, wherein the transparent cover member is comprised of silicon.

4. The transparent cover member of claim 1, wherein the inner standoff wall extends from a bottom of the standoff portion upwards to a height that is higher than the outer shoulder, and is entirely perpendicular to the front plane.

5. The transparent cover member of claim 1, wherein a surface of the front of the transparent cover member is frosted.

6. The transparent cover member of claim 1, further comprising a plurality of retention features that protrude outward from the standoff wall.

7. The transparent cover member of claim 6, wherein the plurality of retention features are formed in a ramp configuration.

8. A transparent cover member for head assembly of a skin treatment device that provides light and heat therapy to a user's skin, comprising:
    a flat front defining a front plane;
    a back that is opposite the flat front, and includes a central portion;
    an outside wall extending down from the front around an entirety of a perimeter of the front; and
    an outside shoulder formed at a bottom of the outside wall, the outside shoulder extending inward from the outside wall to an inner edge of the of the outside shoulder, wherein the inner edge of the outside shoulder meets an outer standoff wall of a standoff portion, the standoff portion extends downward from the inner edge of the outside shoulder in a direction away from the front and the standoff portion surrounds the central portion, wherein the outside shoulder surrounds the standoff portion, the standoff portion having an inner standoff wall that surrounds a hollow space at the back of the transparent cover member, wherein the hollow space is bounded by the inner standoff wall and the back of the top, wherein the entire standoff portion is transparent; and
    wherein the standoff portion extends downward, with respect to the front, farther than the outside shoulder and the central portion.

9. The transparent cover member of claim 8, wherein the transparent cover member is comprised of sapphire glass.

10. The transparent cover member of claim 8, wherein the transparent cover member is comprised of silicon.

11. The transparent cover member of claim 8, wherein the transparent cover member is comprised of material that is selectively transparent for selected wavelengths of infrared light.

12. The transparent cover member of claim 8, wherein the inner standoff wall extends from a bottom of the standoff portion upwards to a height that is higher than the outer shoulder, and is entirely perpendicular to the front plane.

13. The transparent cover member of claim 8, further comprising a plurality of retention features that protrude outward from the standoff wall.

14. The transparent cover member of claim 13, wherein the plurality of retention features are formed in a ramp configuration.

15. A head assembly for a therapeutic device, comprising:
a transparent cover member made entirely of a transparent material and having:
- a front portion having a front surface that is configured to face outward from the skin treatment device;
- a back portion that is opposite the front portion and which includes a central portion;
- a standoff wall that extends downward from the back portion in a direction away from the front portion, and surrounds the central portion of the back portion, and wherein the standoff wall has an outside diameter that is smaller than a diameter of the front portion;
- at least one retention feature that protrudes outward from the standoff wall and which is configured to engage a corresponding retention feature of the therapeutic device to retain the transparent cover member in the therapeutic device, wherein the at least one retention feature is a ramped feature that has a first end and a second end and is ramped in a direction along the standoff wall such the first end is lower than the second end with respect to the front surface; and
- wherein the standoff portion extends downward, with respect to the front surface, farther than both the outside shoulder and the central portion;

a heat element disposed inside the standoff portion; and
a printed circuit board (PCB) disposed under the transparent cover member and having a series of light emitting diodes (LEDs) arranged on the PCB.

16. The head assembly of claim 15, wherein the transparent cover member consists entirely of sapphire glass or silicon.

17. The head assembly of claim 15, wherein the top of the transparent cover member is frosted.

18. The head assembly of claim 15, wherein the standoff portion includes an inner standoff wall that surrounds a hollow space that is bounded by the central portion of the back and the inner standoff wall.

19. The head assembly of claim 18, wherein the inner standoff wall extends from a bottom of the standoff portion upwards to a height that is higher than the outer shoulder, and is entirely perpendicular to the front plane.

* * * * *